(12) United States Patent
Holweg et al.

(10) Patent No.: US 6,375,462 B2
(45) Date of Patent: Apr. 23, 2002

(54) SCREWDRIVER FOR INTRA-ORAL IMPLANTATION

(75) Inventors: Andreas Holweg, Jühnde; Carsten Georg Köhler, Hasselroth-Niedermittlau; Egbert Kremer, Hanau, all of (DE)

(73) Assignee: Degussa AG. (DE)

( * ) Notice: Subject to any disclaimer, the term of this patent is extended or adjusted under 35 U.S.C. 154(b) by 0 days.

(21) Appl. No.: 09/764,138

(22) Filed: Jan. 19, 2001

(30) Foreign Application Priority Data

Feb. 4, 2000 (DE) .......................... 100 05 137

(51) Int. Cl.[7] .............................................. A61C 3/00
(52) U.S. Cl. ...................................... 433/141; 81/177.6
(58) Field of Search .............................. 433/141, 130, 433/163, 173; 81/177.6

(56) References Cited

U.S. PATENT DOCUMENTS

| | | | |
|---|---|---|---|
| 2,501,217 A | * 3/1950 | Hawn | .................. 81/177.6 |
| 4,281,989 A | * 8/1981 | Glover et al. | ............. 433/130 |
| 5,129,823 A | * 7/1992 | Huges | .................. 433/141 |
| 5,572,913 A |  11/1996 | Nasiell | .................. 81/177.6 |
| 6,145,413 A | * 11/2000 | Lin | ............... 81/63.1 |

FOREIGN PATENT DOCUMENTS

| | | |
|---|---|---|
| DE | 86 07 407.5 | 6/1986 |
| DE | 295 12 090 U1 | 1/1996 |

OTHER PUBLICATIONS

German Office Action (German language), dated Apr. 25, 2001.

* cited by examiner

*Primary Examiner*—John J. Wilson
(74) *Attorney, Agent, or Firm*—Smith Gambrell & Russell, LLP

(57) ABSTRACT

A screwdriver for intra-oral implantation features a screwdriver shaft (2), which, at one of its ends, is connected with a hand piece (1) and at its other end, via an angular gear drive (3), with a rotatable tool chuck (4). The screwdriver shaft (2) consists of shaft segments (6) that can, at least partially, be moved in relation to each other and that can be tightened by means of a common longitudinal tightening device for the purpose of fixing them in their relative positions. A drive shaft consists, in the area of the shaft segments (6) of individual shaft pieces that, in the connecting area of two shaft segments (6), are connected via an angular gear for the purpose of torque transmission.

23 Claims, 5 Drawing Sheets

SCREWDRIVER FOR INTRA-ORAL IMPLANTATION

INTRODUCTION AND BACKGROUND

The present invention concerns a screwdriver for intra-oral implantation with a screwdriver shaft, which, at one end, is connected with a hand piece and at the other end, via an angular gear, with a rotatable tool chuck, that is connected, via a drive shaft located inside the shaft of the screwdriver shaft, with a rotating drive located inside the hand piece.

These types of screwdrivers are used to perform the screwing in processes that must be performed on tooth implants inside the oral cavity, and in particular to perform the screwing in processes that need to be performed to attach implant posts and screws to inserted implants. Due to differences in implant accessibility, so far, different types of screwdrivers of a rigid design have been used for this purpose. In a known screwdriver of the aforementioned type the hand piece is connected, via a straight rigid screwdriver shaft, with a 90° angular gear, which is attached to a rotatable tool chuck, into which different types of screwdriver bits can be inserted. Due to the rigid design as a 90° angular screwdriver, adaptability is limited; for implants that are difficult to access, still, additional specialized screwdrivers must be held ready and used.

It is therefore an object of this invention to embody a screwdriver of the aforementioned type in such a manner that it would be suited for all screws occurring in intra-oral implants, in particular also in areas of the oral cavity that are difficult to access.

SUMMARY OF THE INVENTION

According to the invention, the above and other objects can be achieved by a device wherein the shaft of the screwdriver comprises, at least partly, shaft segments that can be shifted in relation to each other and that, for the purpose of fixing them in their positions, can be tightened up by means of a common tightening device that extends longitudinally. The drive shaft in the area of the shaft segments consists of individual drive shaft pieces, which are connected with each other by means of an angular shaft gear, in the area of each connecting area between two shaft segments, are, for the purpose of torque transmission.

The screwdriver shaft, which is flexible prior to tightening the tightening device, can be bent into a shape that may be optimal for each individual situation and be fixed in this shape, so that the tool chuck can be brought into a position which may be the most advantageous one, as the case may be, even for areas within the patient's oral cavity that are difficult to access. Accordingly, all tightening tasks which may occur on dental implants can be performed with one single screwdriver, due to its flexible adjustability. The torque between the individual drive shaft segments is transferred in a positive manner and with only very little torsional elasticity.

BRIEF DESCRIPTION OF THE DRAWINGS

The present invention will be further understood with reference to the accompanying drawings, wherein.

DETAILED DESCRIPTION OF INVENTION

Figure 1:
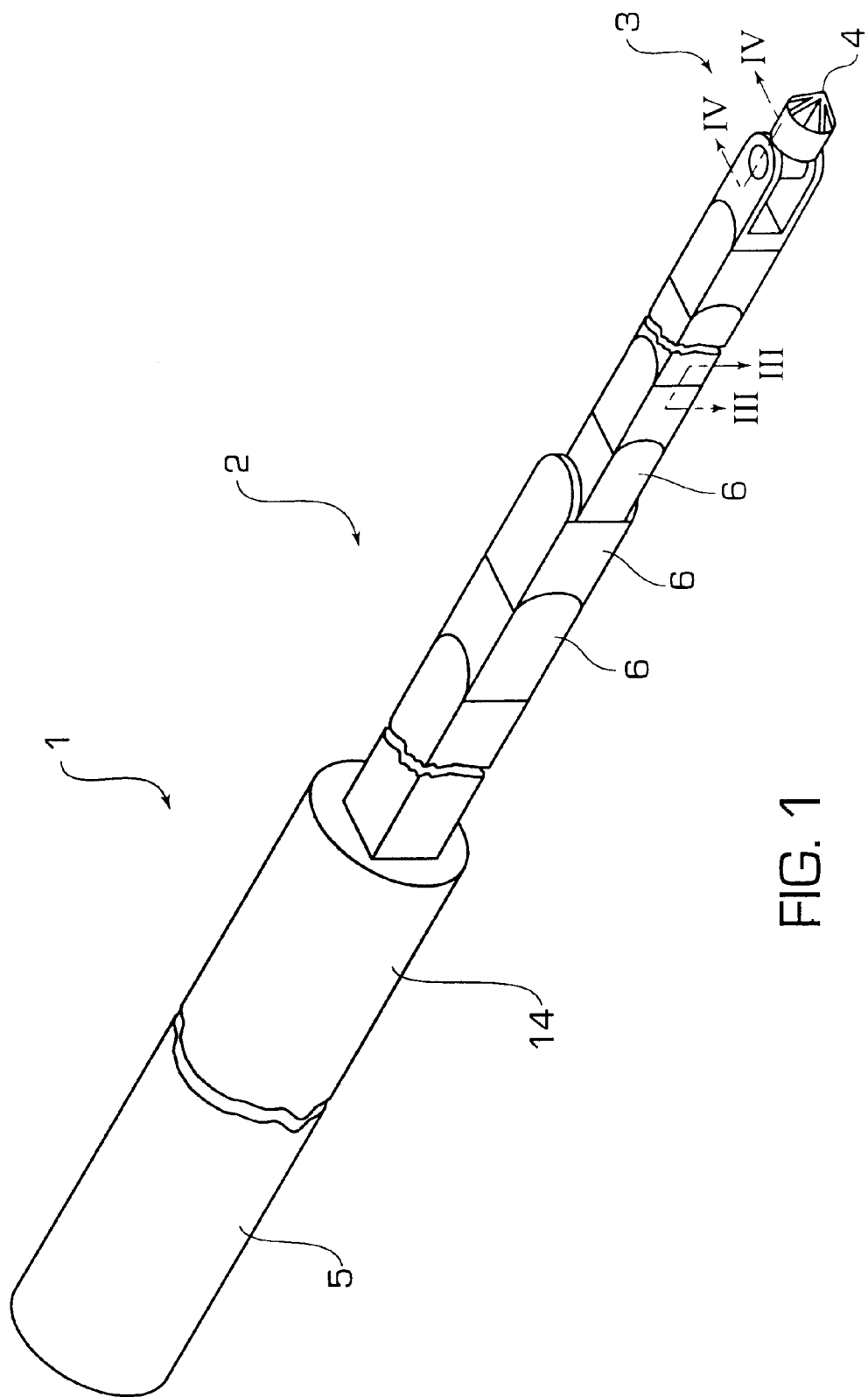
FIG. 1 is a perspective view of a screwdriver for intra-oral implants.

According to a preferred embodiment form of the invention, each shaft segment of the screwdriver features, at one of its ends, a concave gliding surface forming a cylinder segment, and at its other end, a convex gliding surface forming a cylinder segment, with the two cylinder segments featuring identical radii and axial directions that are offset from each other by 90°.

Between each two adjacent shaft segments a link is created that can only be rotated around one axis but which produces a rather stable connection of the two shaft segments when the longitudinal tightening device is tightened. Nonetheless, the screwdriver shaft can be adjusted in any direction, because the links between the shaft segments, which follow one to the next at short intervals, still make a twist possible within the two axes that are at a 90° offset with each other.

Advantageously, the common tightening device of the shaft segments features at least two tightening wires which run through diagonally opposite tightening channels within each shaft segment.

In this manner, a tightening device is implemented in a simple and space-saving fashion that makes it possible to fix the entire screwdriver shaft in any preset position. For this purpose it suffices to put a pulling force on the tightening wires.

According to a preferred embodiment form two pairs of tightening wires are used that are each positioned in traverse positions from each other and that both tightening wires of each pair of tightening wires are connected with each other for length compensation.

In this manner the differences in length of the tightening wires that are conditioned by the one-sided curvature of the screwdriver shaft and which tightening wires are positioned along the external side or the internal side of the curvature, are compensated in a simple way and so that all of the tightening wires contribute to tightening the shaft elements in any curvature position.

Further advantageous embodiments of the idea on which the invention is based are described below.

Below, an embodiment example of the invention, which is illustrated in the drawing, is more closely explained.

The screwdriver for intra-oral implantation shown in FIG. 1 features a hand piece 1, located at the proximate end of the screwdriver, to which an elongated multi-segment screwdriver shaft 2 is connected. At its distal end, which faces away from the hand piece 1 the screwdriver shaft 2 is connected, via an angular gear 3, with a rotatable tool chuck 4, which is configured as a connecting element for different screwdriver bits.

On the hand piece 1, a rotating drive is provided, which in the embodiment shown, includes a rotating handle 5 that is operated manually and that is connected with the rotatable tool chuck 4, via a multi-link drive shaft located within the screwdriver shaft 2 and the angular drive 3, for the purpose of transmitting the torque.

Figure 2:
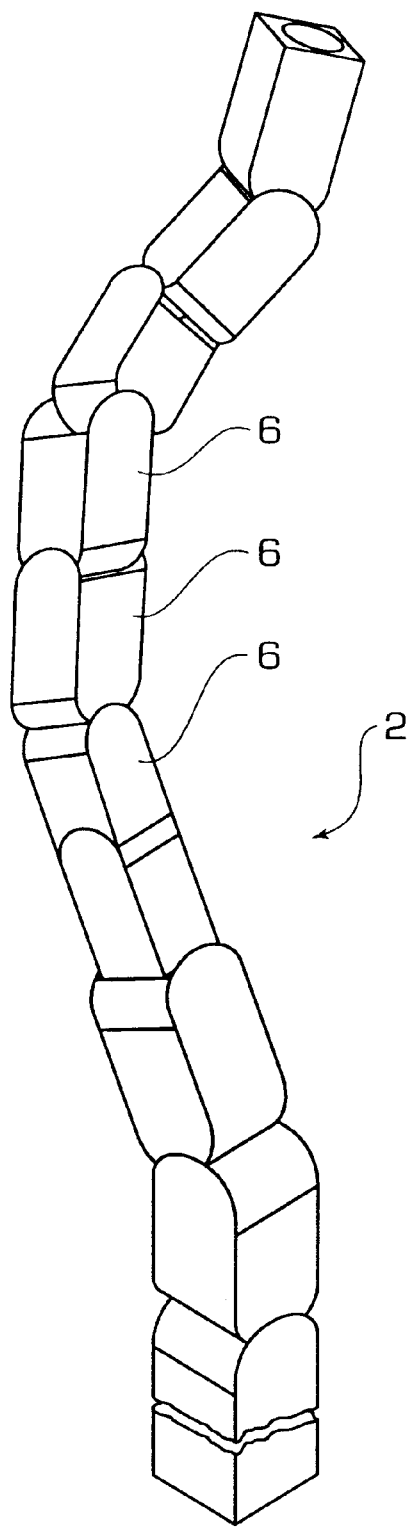
FIG. 2 is a perspective view of the flexible screwdriver shaft of the screwdriver according to FIG. 1 in a multi-curvature position.

The screwdriver shaft 2 consists of a plurality of shaft segments 6 that can be swivelled in relation to each other and that, for this reason, is flexible. The shaft 2 of the screwdriver can be brought into a shape permitted by the mobile linkage of the shaft segments 6 prior to its use, as shown in FIG. 2 in an exemplary fashion.

Figure 3:
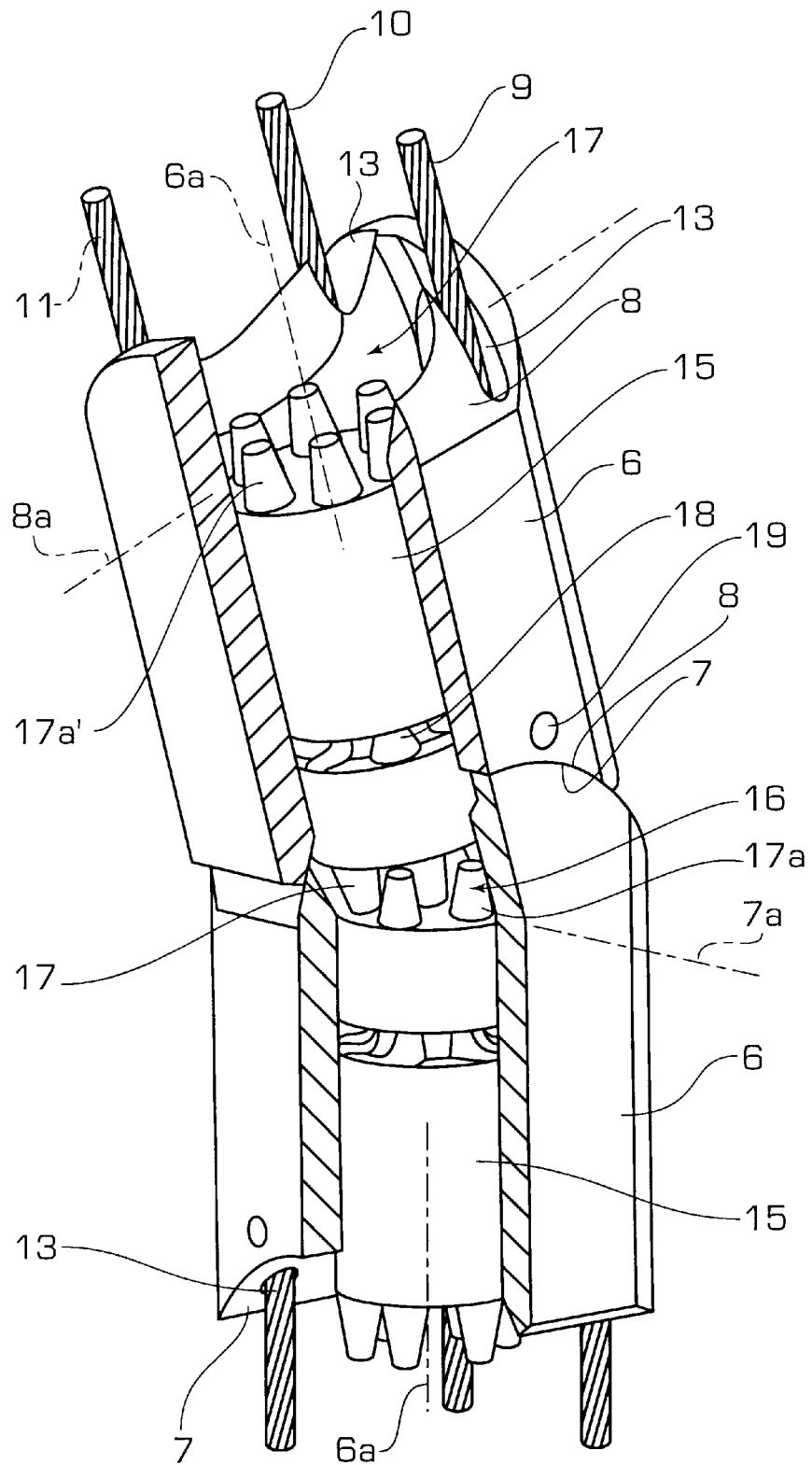
FIG. 3 is a perspective view in partial section of two shaft segments of the screwdriver according to FIG. 1 with the shaft pieces positioned inside.

As is shown in detail in FIG. 3, each shaft segment 6 features, at one of its ends, e.g. the proximate end facing toward the hand piece 1, a concave gliding surface 7, which is configured as a cylinder segment. At its other end, e.g. the distal end facing the tool chuck 4, each shaft segment 6 features a convex gliding surface 8, which is also configured as a cylinder segment. The cylinder segments of the two gliding surfaces 7, 8 have identical radii so that the two gliding surfaces 7, 8 can slide on each other while having full surface contact with each other, as is shown in FIG. 3.

The directions of the two axes 7a and 8a of the two gliding surfaces 7 and 8 are offset against each other, around the longitudinal axis 6a of each shaft segment 6, by 90° each. In this manner, the swiveling direction at the consecutive connecting locations of the shaft segments 6 changes by 90° in a consecutive and alternating manner along the full extent of the screwdriver shaft 2 that in their totality results in spatial flexibility of the multi-link screwdriver shaft 2, as shown in FIG. 2 in an exemplary manner.

A common tightening device serves for the fixation of the screwdriver shaft 2 in the shape selected for each individual case. Four tightening wires 9, 10, 11 and 12 (see FIG. 4) run through the tightening channels 13 that are configured in an axially parallel direction within the tightening segments 6. The tightening channels 13 are, at least at the exit locations at the gliding surfaces 7 and 8, widened in such a manner that the tightening wires 9–12 can enter unobstructed into the tightening channel 13 of each adjacent shaft segment 6 regardless of the swiveling position.

At the tool end of the screwdriver shaft 2 two pairs tightening wires 9 and 11 and 10 and 12, which are located diagonally opposite from each other, are connected with each other in such a manner so as to make length compensation of this pair of tightening wires 9 and 11 or 10 and 12 possible.

In the area of the hand piece 1 all of the tightening wires 9–12 are connected with a common tightening element (not shown here), which can be longitudinally moved inside the hand piece by means of a gear screw. In this way all of the tightening wires can be tightened for fixation and loosening of the screwdriver shaft 2. The gear screw of the tightening element is actuated by rotating a rotating ring 14 on the hand piece 1 (see FIG. 1).

The drive shaft extending throughout the entire screwdriver shaft 2 consists, in the area of the swiveling shaft segment 6, of individual shaft elements 15 (FIG. 3), which within each connecting area of two shaft segments 6, are moveably connected with each other via an angular gear drive 16 for the purpose of transmitting the torque. Each shaft piece 15 is rotatably supported within the correlated shaft segment 6 and features a pinion gear 17 consisting of axially parallel tapered driving teeth 17a, 17a'. The pinion gears 17 of adjacent shaft pieces 15 engage each other in a positive fashion. The tapered shape of the gear teeth 17a makes it possible to maintain the gear engagement, even when the adjacent shaft pieces 6 are angled off as shown in FIG. 3.

Each shaft piece 15 features a circumferential groove 18 in which a cross pin 19, which is attached inside the shaft segment 6, tangentially engages. In this manner the rotatable shaft piece 15 is fixed inside the shaft segment 6 in an axial direction.

Figure 4:
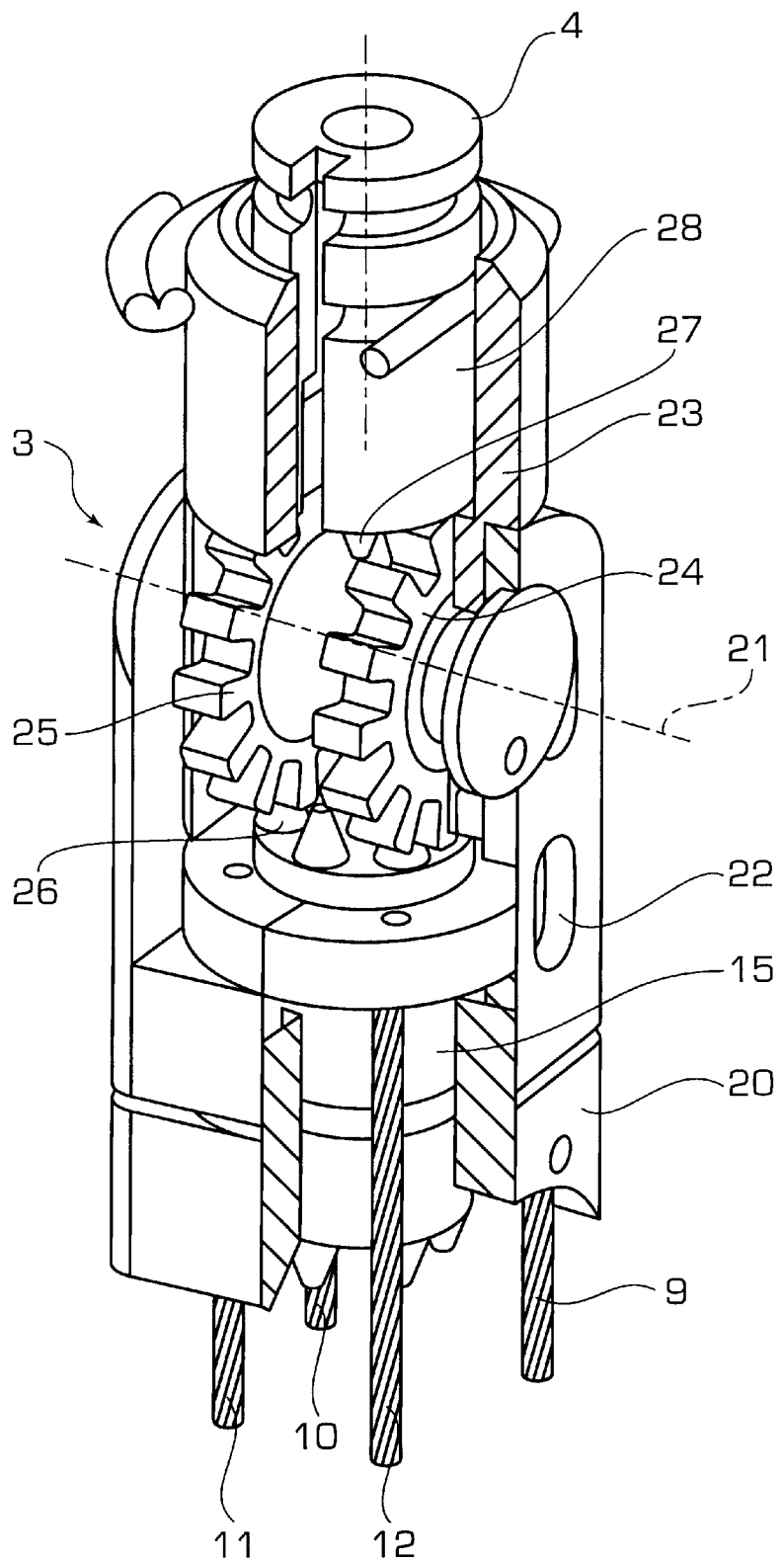
FIG. 4 is a perspective view in partial section of an angular gear and the tool-side end of the screwdriver shaft.
Figure 5:
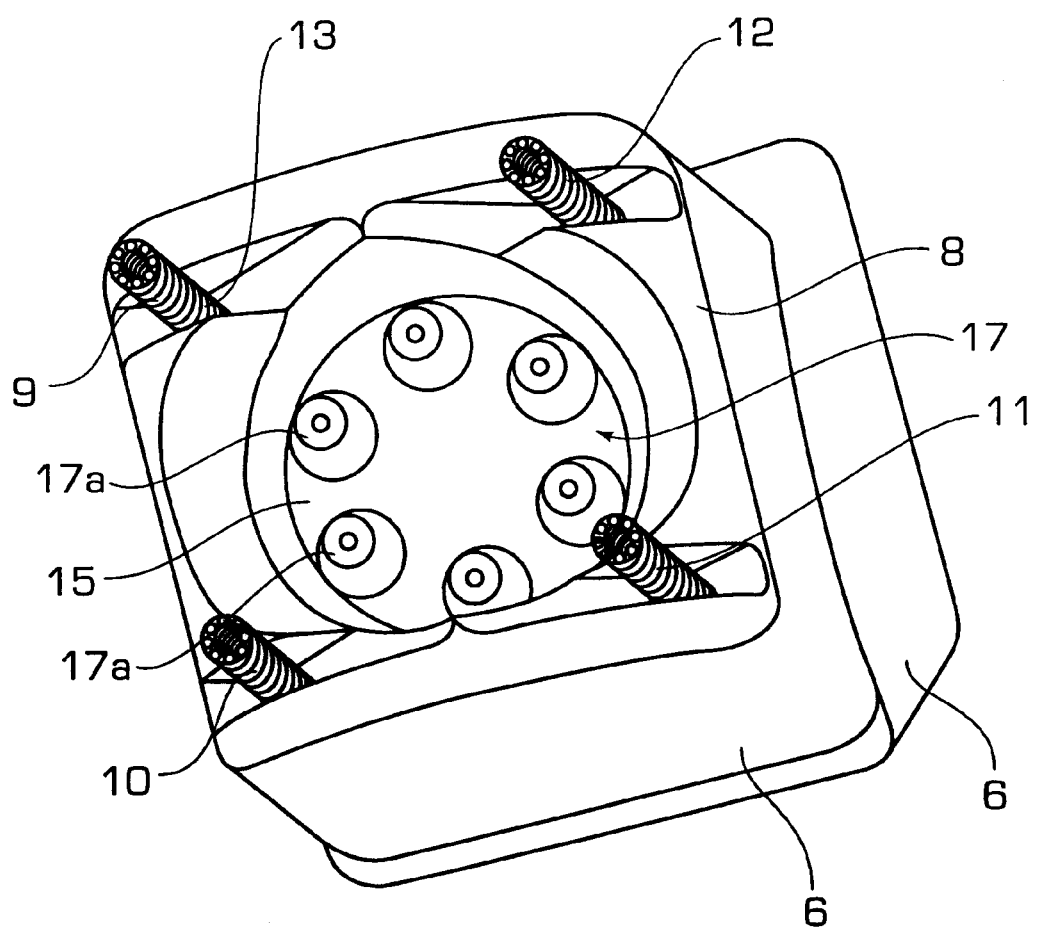
FIG. 5 is a perspective view of a cross section of the screwdriver at the connecting area between two shaft segments.

The angular gear 3, which joins the tool chuck 4 and is shown in FIG. 4 in detail, is designed to be a pivoting angular gear making it possible for the tool chuck 4 (shown only partly in FIG. 4) to pivot relative to the final segment 20 of the screwdriver shaft 2 around a common traverse axis 21. Two housing parts 22 and 23 of the angular gear 3 can be pivoted around the common traverse axis 21.

Two transmission gears 24, 25 can be independently rotated around the traverse axis 21 inside the pivoting angular gear 3 and each engage a pinion gear 26 and 27 of the adjacent shaft pieces 15 and 28. Even if the pivoting angular gear 3 is pivoted out of the straight through-going position shown in FIG. 4 around the traverse axis 21, the rotating movement of the shaft piece 15 is transmitted via the pinion gear 26 and the two counter-directionally driven transmission gears 24, 25 to the pinion gear 27 of the shaft piece 28 that is connected with the tool chuck 4.

Further variations and modifications of the foregoing will be apparent to those skilled in the art and are intended to be encompassed by the claims appended hereto.

German priority application 100 05 137.5 is relied on and incorporated herein by reference.

What is claimed is:

1. A screwdriver for intra-oral implantation comprising:
   a screwdriver shaft including a plurality of interconnected shaft segments;
   a hand piece connected to a first end of said screwdriver shaft;
   a tool chuck connected at a second end of said screwdriver shaft; and
   a common longitudinal tightening device including at least two tightening wires travelling through diagonally opposite tightening channels in each of said shaft segments for tightening and fixing said plurality of shaft segments in their respective positions.

2. The screwdriver according to claim 1, wherein said tool chuck is rotatable.

3. The screwdriver according to claim 1, wherein said plurality of shaft segments are movable in relation to each other.

4. The screwdriver according to claim 3 wherein a drive shaft is centrally located within an interior space defined by said screwdriver shaft.

5. The screwdriver according to claim 4, wherein said rotatable tool chuck is interconnected via said drive shaft to a rotating drive.

6. The screwdriver according to claim 5, wherein said rotating drive is located within an interior hollow enclosed by said hand piece.

7. The screwdriver according to claim 6, wherein said plurality of shaft segments are interconnected via individual shaft pieces.

8. The screwdriver according to claim 7, wherein said shaft pieces of adjacent shaft segments include an association with an angular gear drive for torque transmission.

9. The screwdriver according to claim 8, wherein each shaft segment includes a concave gliding surface at one of its ends and a convex gliding surface at its other end.

10. The screwdriver according to claim 9, wherein said convex and said concave gliding surfaces form cylindrical segments.

11. The screwdriver according to claim 10, wherein said cylindrical segments include identical radii and axial directions and are offset from each other by 90 degrees.

12. The screwdriver according to claim 11, wherein said longitudinal common tightening device includes at least two tightening wires.

13. The screwdriver according to claim 12, wherein two pairs of said tightening wires are positioned in a diagonal spatial orientation in relation to each other.

14. The screwdriver according to claim 13, wherein said two tightening wires of each pair are connected with each other at one end for the purpose of length compensation.

15. The screwdriver according to claims 14, wherein all tightening wires are connected with a tightening piece that is positioned within said interior hollow of said hand piece.

16. The screwdriver according to claim 15, wherein said tightening wires are longitudinally adjusted via a gear screw.

17. The screwdriver according to claim 16, wherein each shaft piece is rotatably supported within a predetermined interior area within said corresponding shaft segment.

18. The screwdriver according to claim 17, wherein each shaft piece includes a pinion gear at both of its ends.

19. The screwdriver according to claim 18, wherein each pinion gear includes axially parallel tapered drive teeth, said pinion gears of adjacent shaft pieces engaging each other in a positive fashion.

20. The screwdriver according to claim 19, wherein said angular gear drive adjacent to said rotatable tool chuck includes a first and second housing parts that can be pivoted around a common traverse axis.

21. The screwdriver according to claim 20, including at least one transmission gear positioned to rotate around said common traverse axis and engaging said pinion gear of the corresponding one of said shaft pieces.

22. The screwdriver according to claim 21, wherein two transmission gears are rotated independently from each other around said common traverse axis within said angular gear drive.

23. The screwdriver according to claim 3, wherein said rotatable tool chuck is connected to said second end of said screwdriver shaft via an angular gear drive.

* * * * *